United States Patent
Kimura (10) Patent No.: US 8,645,081 B2
(45) Date of Patent: Feb. 4, 2014

(54) DEVICE AND METHOD OF EXAMINING ABSORPTION OF INFRARED RADIATION

(75) Inventor: Noriaki Kimura, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 384 days.

(21) Appl. No.: 13/055,439

(22) PCT Filed: Jul. 21, 2009

(86) PCT No.: PCT/JP2009/003398
§ 371 (c)(1),
(2), (4) Date: Jan. 21, 2011

(87) PCT Pub. No.: WO2010/010684
PCT Pub. Date: Jan. 28, 2010

(65) Prior Publication Data
US 2011/0130973 A1    Jun. 2, 2011

(30) Foreign Application Priority Data
Jul. 22, 2008    (JP) .................................. 2008-188288

(51) Int. Cl.
G06F 19/00    (2011.01)
G01N 21/00    (2006.01)

(52) U.S. Cl.
USPC ............................................. 702/24; 356/437

(58) Field of Classification Search
CPC ..................................................... G01N 21/00
USPC ........................................... 702/24; 356/437
See application file for complete search history.

(56) References Cited

U.S. PATENT DOCUMENTS

| | | | |
|---|---|---|---|
| 4,083,560 A | * | 4/1978 | Kikuchi et al. .................... 463/5 |
| 5,015,099 A | * | 5/1991 | Nagai et al. .................... 356/437 |
| 5,317,376 A | * | 5/1994 | Amzajerdian et al. ....... 356/28.5 |

(Continued)

FOREIGN PATENT DOCUMENTS

| JP | 2003-247941 A | 9/2003 |
|---|---|---|
| JP | 2005-157601 A | 6/2005 |

(Continued)

OTHER PUBLICATIONS

Non-Patent Document 1: Wolfgang Demtroder, "Laser Spectroscopy", Springer Press, p. 370.

(Continued)

Primary Examiner — Mohamed Charioui
Assistant Examiner — Joseph J Yamamoto
(74) Attorney, Agent, or Firm — Global IP Counselors, LLP (57) ABSTRACT

A light absorption examining device includes a laser light source that emits the pulse laser beam, a measuring unit that retains the measuring object and irradiates the measuring object with the pulse laser beam, a light receiving unit that receives the pulse laser beam transmitted through the measuring object and outputs a light receiving signal, a pulse generator that produces a single rectangular pulse at a time when a signal level of the light receiving signal output from the light receiving unit intersects a set threshold, a laser driver that supplies the produced rectangular pulse to the laser light source to emit the pulse laser beam, and a control/processing unit that determines an accumulated delay time and examines absorption of the pulse laser beam by the measuring object using the determined accumulated delay time, the accumulated delay time representing a delay in a production timing of the rectangular pulse.

11 Claims, 4 Drawing Sheets

(56) References Cited

U.S. PATENT DOCUMENTS

| | | | |
|---|---|---|---|
| 6,191,861 B1 * | 2/2001 | McBranch et al. | 356/432 |
| 6,573,493 B1 * | 6/2003 | Futami et al. | 250/288 |
| 2006/0072118 A1 | 4/2006 | Chan et al. | |
| 2006/0244629 A1 | 11/2006 | Miyazaki et al. | |

FOREIGN PATENT DOCUMENTS

| | | |
|---|---|---|
| JP | 2005-535411 A | 11/2005 |
| JP | 2006-105720 A | 4/2006 |
| WO | WO-2004/016171 A1 | 2/2004 |

OTHER PUBLICATIONS

Non-Patent Document 2: Wolfgang Demtroder, "Laser Spectroscopy", Springer Press, p. 382-384.

* cited by examiner

DEVICE AND METHOD OF EXAMINING ABSORPTION OF INFRARED RADIATION

CROSS-REFERENCE TO RELATED APPLICATIONS

This U.S. National stage application claims priority under 35 U.S.C. §119(a) to PCT Patent Application PCT/JP2009/003398 filed Jul. 21, 2009 and to Japanese Patent Application No. 2008-188288 filed in Japan on Jul. 22, 2008. The entire contents of PCT Patent Application PCT/JP2009/003398 and Japanese Patent Application No. 2008-188288 are hereby incorporated herein by reference.

TECHNICAL FIELD

The present invention relates to a device and a method, in which a measuring object is irradiated with a pulse laser beam having wavelength in an infrared region and light absorption by the measuring object is examined by measuring the pulse laser beam transmitted through the measuring object. Particularly the invention relates to a technical field in which a concentration of trace gas that is one of the measuring object is accurately detected at high speed from infrared radiation absorption at the specific wavelength.

BACKGROUND ART

Currently a gas analyzer is used to measure a concentration of gas of the ppm order contained in air. One of a controlled-potential electrolysis method, a chemiluminescent method, and a level method (Salzman reagent method) is adopted in the gas analyzer. However, in the methods, because the measurement is not performed before the air containing the gas of the examination object is accommodated in a special cell, unfortunately the flowing air containing the gas of the examination object cannot be examined in real time.

A multiple reflection cell method (Wolfgang Demtroder, "Laser Spectroscopy", Springer Press, P370) or a cavity ring-down method (Wolfgang Demtroder, "Laser Spectroscopy", Springer Press, P838) can be cited as an example of a method of measuring the gas concentration using the laser beam which has wavelength in the infrared region. A cell is used in measuring the gas concentration, and the cell including reflecting surfaces at both end faces has a long and thin space in which the measuring object is accommodated. The cell is irradiated with the laser beam along a longitudinal direction of the space. The reason the cell having the long and thin space is used is that an optical path of the laser beam in the cell gets lengthened, for example, the optical path is set to 1 to 15 m, enough to accurately examine the trace gas having the low concentration when the measuring object is contained in a low gas concentration of the ppm order in air.

Figure 7:
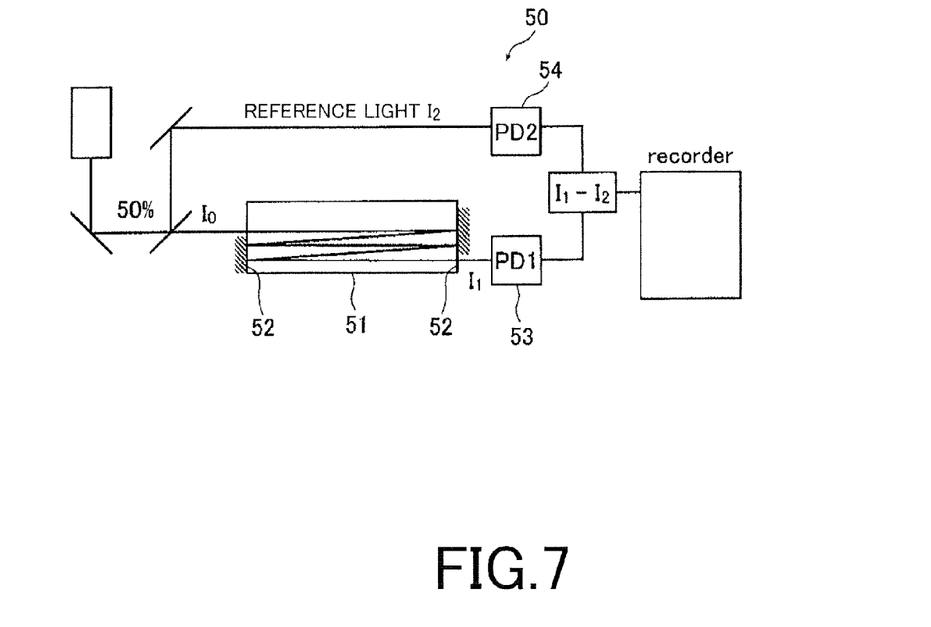
FIG. 7 is a schematic configuration diagram of a conventional device in which a multiple reflection cell method is adopted.

FIG. 7 schematically illustrates a conventional device 50 in which the multiple reflection cell method is adopted. In the device 50, a cell 51 having a long and thin space is used, and mirrors 52 having high reflectances are provided at both ends of the cell 51. The laser beam incident to the cell 51 is reflected many times at both the end faces in which the mirrors 52 are provided, which allows the optical path of the laser beam to be lengthened. A detector 53 detects the laser beam after the laser beam is reflected plural times by the mirrors 52, and a detector 54 detects reference light that is obtained by separating the laser beam immediately before the laser beam is incident to the cell 51. A difference between signal intensity obtained by the detector 53 and signal intensity obtained by the detector 54 is determined to examine the gas. When the laser beam is reflected by the mirror to lengthen the optical path length, an amount of the laser beam absorbed by the gas of the measuring object is increased, so that the absorption amount of the laser beam can be examined even in the trace gas.

Figure 8:
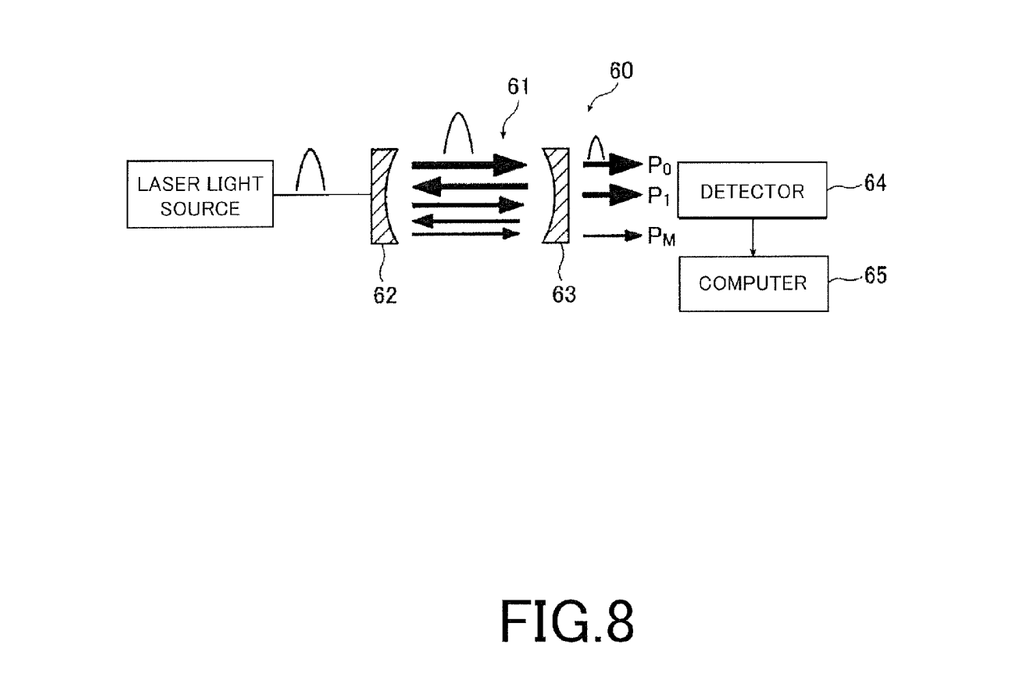
FIG. 8 is a schematic configuration diagram of a conventional device in which a cavity ring-down method is adopted.

FIG. 8 schematically illustrates a conventional device 60 in which the cavity ring-down method is adopted. In the device 60, concave minors 62 and 63 are provided at both end faces of a long and thin space 61, the laser beam is confined in the space 61 to lengthen the optical path of the laser beam. Laser beams $p_0, p_1, \ldots$, and $p_N$ are taken out from the concave mirror 63 by a detector 64 according to the number of reflection times, and a computer 65 computes a gas absorption amount. Thus, the optical path of the laser beam can be lengthened to increase the amount of laser beam absorbed by the gas of the measuring object using the concave mirrors 62 and 63, and the absorption amount of the laser beam can be examined even in the trace gas.

However, in the device 50 illustrated in FIG. 7, the mirror having the high reflectance is hardly prepared, and the width of a light flux of the laser beam is hardly kept constant in the long optical path. In the device 60 illustrated in FIG. 8, the mirror having the high reflectance is hardly prepared similarly to the device 50 illustrated in FIG. 7. In addition, because the concave mirror having the high reflectance is used, unfortunately a laser generating device having high power output is required to introduce the laser beam from the end face into the long and thin space.

Accordingly, the special cell is required to measure the gas concentration. In the device in which the multiple reflection method or the cavity ring-down method is performed using the infrared laser beam, it is necessary to introduce the gas to be measured into the cell in addition to the difficulty of preparing the mirror having the high reflectance and the difficulty of introducing the laser beam. Therefore, a chemical reaction product is hardly measured on site in real time.

SUMMARY OF THE INVENTION

Problem to be Solved by the Invention

In view of the foregoing, an object of the invention is to provide a light absorption examining device and a light absorption examining method, in which the laser absorption method is adopted, a special cell is not used, and the light absorption of the measuring object can correctly be examined in real time without lengthening the optical path of the laser beam.

To solve the above mentioned problem, the present invention provides a light absorption examining device that examines pulse laser beam absorption when a measuring object is irradiated with a pulse laser beam and the pulse laser beam is transmitted through the measuring object. The light absorption examining device includes:

a laser light source that emits the pulse laser beam according to a supplied driving pulse;

a measuring unit that retains the measuring object and irradiates the measuring object with the pulse laser beam to cause the pulse laser beam to transmit through the measuring object;

a light receiving unit that receives the pulse laser beam transmitted through the measuring object and outputs a light receiving signal;

a pulse generator that produces a single rectangular pulse at a time when a signal level of the light receiving signal output from the light receiving unit intersects a set threshold;

a laser driver that supplies the produced rectangular pulse as the driving pulse to the laser light source in order to drive the laser light source to emit the pulse laser beam from the laser light source every time the produced rectangular pulse is supplied, and drives the laser light source to emit a single pulse laser beam; and a control/processing unit that determines an accumulated delay time and examines absorption of the pulse laser beam by the measuring object using the determined accumulated delay time, the accumulated delay time representing a delay in a production timing of the rectangular pulse caused by reduction of light intensity due to absorption of the pulse laser beam during a period between a start-up driving pulse and a latest rectangular pulse that is produced when a number of production times of the rectangular pulse in the pulse generator reaches a predetermined number, after the start-up driving pulse for starting the emission of the pulse laser beam is supplied to the laser driver to drive the laser light source to emit the pulse laser beam and the rectangular pulse is supplied a plurality of times from the pulse generator to drive the laser light source to emit the pulse laser beam the plurality of times.

In the device, it is preferable that the measuring object is gas contained in a gaseous body, the control/processing unit includes a reference table representing a correspondence relationship between a concentration of the gas and a delay time in the production timing of the rectangular pulse when light is absorbed by the gas, and the control/processing unit computes the concentration of the gas from the determined accumulated delay time using the reference table.

It is alternatively preferable that the control/processing unit controls a wavelength of the laser beam emitted from the laser light source to be variable, the control/processing unit sets a first wavelength in which the accumulated delay time is maximized and a second wavelength in which the accumulated delay time is minimized to the laser light source, and the control/processing unit examines infrared radiation absorption by the measuring object using a difference between the accumulated delay time determined at the first wavelength and the accumulated delay time obtained at the second wavelength.

It is also preferable that the device further includes: a beamsplitter that splits the pulse laser beam emitted from the laser light source before the pulse laser beam is incident to the measuring unit; an intensity sensor that receives the split pulse laser beam to sense light intensity of the pulse laser beam; and a threshold adjusting unit that adjusts the threshold in order to compensate a fluctuation of the light intensity of the pulse laser beam based on the light intensity obtained in the intensity sensor. Then, the threshold adjusting unit preferably sets the threshold such that the threshold is proportional to the light intensity obtained in the intensity sensor.

The pulse laser beam is exemplified by a laser beam having wavelength in an infrared region.

The present invention also provides a light absorption examining method of examining pulse laser beam absorption when a measuring object is irradiated with a pulse laser beam and the pulse laser beam is transmitted through the measuring object. The light absorption examining method includes:

a first step of driving a laser light source to emit the pulse laser beam using a driving pulse supplied to emit the pulse laser beam and of receiving the pulse laser beam transmitted through the measuring object to obtain a light receiving signal;

a second step of producing a single rectangular pulse at a time when a signal level of the obtained light receiving signal intersects a set threshold;

a third step of supplying the produced rectangular pulse as the driving pulse to the laser light source in order to emit the pulse laser beam; and a fourth step of repeating the first step, the second step, and the third step to determines an accumulated delay time, and of examining absorption of the pulse laser beam by the measuring object using the accumulated delay time, the accumulated delay time representing a delay in a production timing of the rectangular pulse caused by reduction of light intensity due to absorption of the pulse laser beam during a period between a start-up driving pulse and a latest rectangular pulse that is produced when a number of production times of the rectangular pulse in the pulse generator reaches a predetermined number.

In the method, it is preferable that a first wavelength in which the accumulated delay time is maximized and a second wavelength in which the accumulated delay time is minimized are set to the laser light source in the first step, and infrared radiation absorption by the measuring object is examined using a difference between the accumulated delay time determined at the first wavelength and the accumulated delay time obtained at the second wavelength in the fourth step.

It is also preferable that the pulse laser beam emitted from the laser light source is split before the pulse laser beam is incident to the measuring object in the first step, and the light absorption examining method further includes a fifth step of receiving the split pulse laser beam to sense light intensity of the pulse laser beam and of adjusting the threshold in order to compensate a fluctuation of the light intensity of the pulse laser beam based on the sensed light intensity.

The pulse laser beam is exemplified by a laser beam having wavelength in an infrared region.

Effect of the Invention

In the present invention, when the number of times of the rectangular pulse produced by the pulse generator reaches the predetermined number, the accumulated delay time is determined and the light absorbed by the measuring object is examined using the accumulated delay time. The accumulated delay time represents a delay of timing of the rectangular pulse production and is effected by the reduction of the light intensity due to the pulse laser beam absorption from the start-up driving pulse to the rectangular pulse. Accordingly, the examination can be performed with high accuracy compared with the conventional method of determining the light absorption of the measuring object from a decrease of the amplitude of the light receiving signal. A part of the pulse laser beam is split by the beamsplitter before the pulse laser beam is incident to the measuring unit, the split pulse laser beam is measured with the intensity sensor, and the threshold used in the pulse generator is adjusted based on the light intensity obtained by the intensity sensor. Therefore, even if the light intensity of the pulse laser beam varies in each time of the emission, the delay time can correctly be determined to perform the high-accuracy examination.

BRIEF DESCRIPTION OF DRAWINGS

FIGS. 3 (*a*) to (*e*) are timing charts of signals produced by a device illustrated in FIG. 1.

BEST MODE FOR CARRYING OUT THE INVENTION

A light absorption examining device and a light absorption examining method according to embodiments of the invention will be described below.

Figure 1:
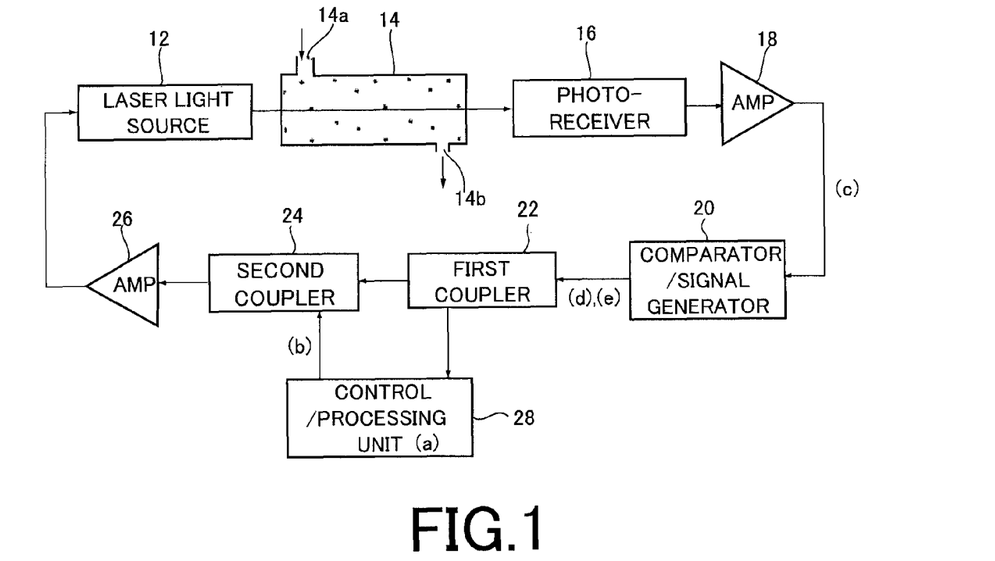
FIG. 1 is a schematic configuration diagram of a light absorption examining device according to an embodiment of the invention.

FIG. 1 is a schematic configuration diagram of a trace gas examining device 10 that is of a light absorption examining device according to an embodiment of the invention in which an infrared radiation absorption method is adopted.

The examining device 10 includes a laser light source 12, a measuring unit 14, a photo-receiver 16, a light receiving signal amplifier 18, a comparator/signal generator (hereinafter simply referred to as a comparator) 20, a first coupler 22, a second coupler 24, a driving signal amplifier 26, and a control/processing unit 28. The components of the laser light source 12, the measuring unit 14, the photo-receiver 16, the light receiving signal amplifier 18, the comparator 20, the third coupler 22, the second coupler 24, and the driving signal amplifier 26 are provided in a loop circuit in the examining device 10.

The laser light source 12 emits a single pulse laser beam having wavelength in an infrared region according to a supplied single driving pulse. For example, a Quantum Cascade Laser (QCL) light source that emits a laser beam having any wavelength region from an infrared region to a terahertz region is used, and preferably a laser light source in which a laser oscillator is set within a range of a predetermined infrared region is used. The gas molecule of the examination object has many absorption spectral lines in the infrared region, where the absorption of various gas molecules can be measured. The laser light source 12 is configured such that the control/processing unit 28 controls the wavelength of the emitted laser beam to be variable. The emission time of the pulse laser beam from the laser light source 12 is controlled in a range of one nanosecond to tens nanoseconds, for example.

The measuring unit 14 includes a cylindrical vessel having a space in which a gaseous body containing a certain gas component of the examination object is accommodated. In the measuring unit 14, light transmission windows are provided at both ends such that the pulse laser beam from the laser light source 12 passes from one end of the cylindrical vessel toward the other end. The cylindrical vessel is not necessarily a sealed vessel, but a gas inlet port 14a and a gas exhaust port 14b are provided such that the gaseous body containing the gas component of the examination object can be examined while flowing in the cylindrical vessel. Since the concentration of the gas component of the examination object contained in the gaseous body can be measured in substantially real time, the flowing gaseous body can be used for the examination as just described.

The cylindrical vessel is not required to have a length of 1 to 15 m along a laser beam traveling direction unlike the conventional cylindrical vessel, but the cylindrical vessel may have the length of several centimeters to one meter.

The photo-receiver 16 receives the pulse laser beam transmitted through the gaseous body containing the gas component that is of the examination object in the cylindrical vessel, and the photo-receiver 16 outputs a light receiving signal. For example, a photoconductive element (MCT element) having a light receiving surface made of HgCdTe is preferably used as the photo-receiver 16. The pulse laser beam that is received by the photo-receiver 16 after transmitted through the measuring unit 14 has light intensity reduced due to the light absorption of the gas component.

The light receiving signal amplifier 18 amplifies the light receiving signal output from the photo-receiver 16. A well-known amplifier is used as the light receiving signal amplifier 18. The comparator 20 compares the light receiving signal, which is output from the photo-receiver 16 and amplified, to a previously set threshold, and produces a rectangular pulse at the time a signal level of the light receiving signal intersects the set threshold. The comparator 20 corresponds to the pulse generator of the invention.

The first coupler 22 acts as a divider that divides the rectangular pulse produced by the comparator 20. For example, a 3-dB coupler or a 6-dB coupler is used as the first coupler 22. A portion of the rectangular pulse divided by the first coupler 22 is supplied to the control/processing unit 28. On the other hand, the rest portion of the rectangular pulse is supplied to the second coupler 24.

The second coupler 24 passes the rectangular pulse supplied from the first coupler 22 and supplies the rectangular pulse to the driving signal amplifier 26. In order to pass a start-up driving pulse supplied from the control/processing unit 28 to the driving signal amplifier 26, the second coupler 24 couples a signal line from the control/processing unit 28 to a signal line that connects the first coupler 22 and the driving signal amplifier 26.

The driving signal amplifier 26 amplifies the rectangular pulse supplied from the second coupler 24 and the start-up driving pulse to a predetermined level, and supplies the rectangular pulse and the start-up driving pulse as the driving pulse to the laser light source 12. The driving signal amplifier 26 corresponds to the laser driver of the laser light source 12. The laser light source 12 emits the pulse laser beam in response to the driving pulse every time the driving pulse is supplied.

The control/processing unit 28 examines the light absorption of the gas component while controlling the start and end of the gas component examination. For example, the control/processing unit 28 includes a computer. An RF switch (not illustrated) is provided in part of the loop circuit illustrated in FIG. 1, and the control/processing unit 28 performs the control such that the RF switch is turned off when the examination is ended. The control/processing unit 28 produces the start-up driving pulse such that the laser light source 12 starts to emit the pulse laser beam. The control/processing unit 28 obtains the rectangular pulse supplied from the first coupler 22 to measure an accumulated delay time, and examines the infrared radiation absorption of the gas component of the examination object using the measured accumulated delay time. The accumulated delay time occurs due to the light absorption in an elapsed time between the latest obtained rectangular pulse and the start-up driving pulse when the number of producing times of the rectangular pulse produced by the comparator 20 reaches a predetermined number. The accumulated delay time represents a time difference in which the elapsed time in the absence of the light absorption is subtracted from the elapsed time in the presence of the light absorption.

Figure 2:
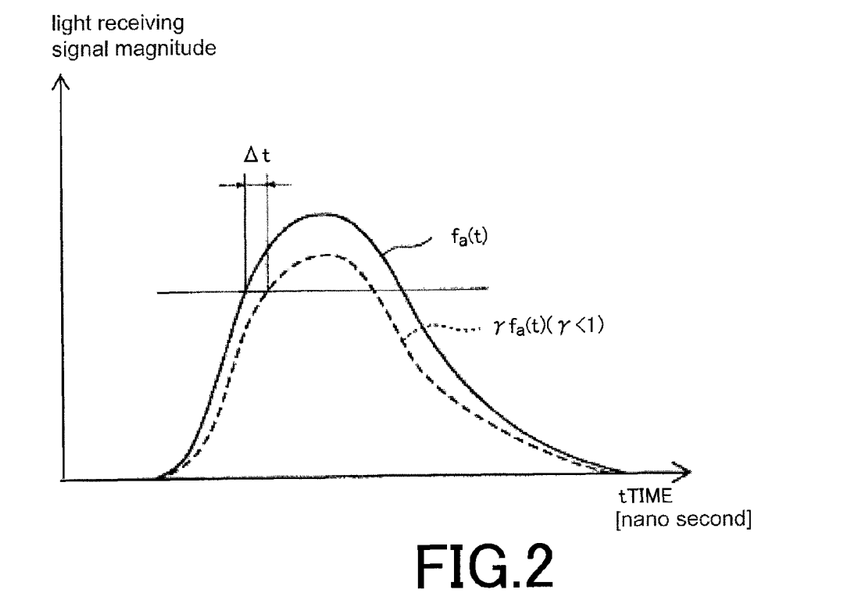
FIG. 2 is a view explaining a delay time obtained by the light absorption examining device of the embodiment.

Specifically, as illustrated in FIG. 2, the light intensity of the light receiving signal supplied to the comparator 20 is reduced compared with a light receiving signal $f_a(t)$ in the absence of the infrared radiation absorption. FIG. 2 illustrates the light receiving signal (solid line) in the absence of the infrared radiation absorption and the light receiving signal (dotted line) in the presence of the infrared radiation absorption. Because the comparator 20 produces the rectangular pulse when the amplified light receiving signal intersects the predetermined threshold, the time the rectangular pulse is produced is delayed by $\Delta t$ for a light receiving signal $\gamma \cdot f_a(t)$ ($\gamma<1$) in which the light intensity is reduced due to the infrared radiation absorption. On the other hand, after the control/processing unit 28 produces the start-up driving pulse to emit the pulse laser beam from the laser light source 12, the comparator 20 produces the rectangular pulse using the light receiving signal produced by the photo-receiver 16. The rectangular pulse produced by the comparator 20 is supplied as the driving pulse of the laser light source 12 through the first coupler 22, the second coupler 24, and the driving signal amplifier 26. Therefore, the emission of the pulse laser beam from the laser light source 12 and the production of the rectangular pulse are repeated. During the repetition, the light intensity of the laser beam transmitted through the vessel of the measuring unit 14 is reduced. Therefore, assuming that N is the number of repetition times of the rectangular pulse production, the time the rectangular pulse is produced is delayed by $N\Delta t$ in total compared with the absence of the light absorption. $N\Delta t$ is the accumulated delay time. The number of times of the pulse production is counted with a counter circuit (not illustrated) and the like, and an Nth-time rectangular pulse is supplied to the control/processing unit 28 when the counting result is N times. When the counting result does not reach the N times, the first coupler 22 is set such that the rectangular pulse is transmitted to the second coupler 24.

The control/processing unit 28 measures the accumulated delay time, which represents a delay of the production of the Nth-time rectangular pulse and occurs in the elapsed time from the start-up driving pulse to the Nth-time rectangular pulse. The control/processing unit 28 computes a one-time delay time from the accumulated delay time, examines the infrared radiation absorption of the gas component, and determines the concentration of the gas component. Specifically, the concentration of the gas component is computed from the delay time $\Delta t$ which represents a delay of the production of a single rectangular pulse using a previously prepared reference table which represents a correspondence relationship between a delay time $\Delta t=(T-T')/N$ and a gas concentration. The delay time $\Delta t=(T-T')/N$ computed from a difference between an elapsed time T from the start-up driving pulse to the Nth-time rectangular pulse and an elapsed time T' which is supposed in absence of the infrared radiation absorption of the gas component. The elapsed time T' which is supposed in absence of the infrared radiation absorption of the gas component includes a transmission time on the signal line for the light receiving signal and the rectangular pulse in addition to the time pulse laser beam passes through the measuring unit 14.

Alternatively, instead of the above-described processing, the control/processing unit 28 may perform the following processing. The control/processing unit 28 measures the accumulated delay time at a first wavelength in which the accumulated delay time becomes the maximum and at a second wavelength in which the accumulated delay time becomes the minimum and sets a difference between the accumulated delay time (maximum accumulated delay time) at the first wavelength and the accumulated delay time (minimum accumulated delay time) at the second wavelength to the original accumulated delay time. Using the reference table, the control/processing unit 28 examines the infrared radiation absorption of the gas component from a delay time $\Delta t$ in the one-time rectangular pulse obtained from the original accumulated delay time. Thus, the accumulated delay time in the infrared radiation absorption and the accumulated delay time in absence of the infrared radiation absorption are obtained by utilizing the change in wavelength of the pulse laser beam. Therefore, the processing result can be high accurate. The wavelength in which the accumulated delay time becomes the maximum and the wavelength in which the wavelength becomes the minimum are known when the gas component of the measuring object is identified.

Figure 3:
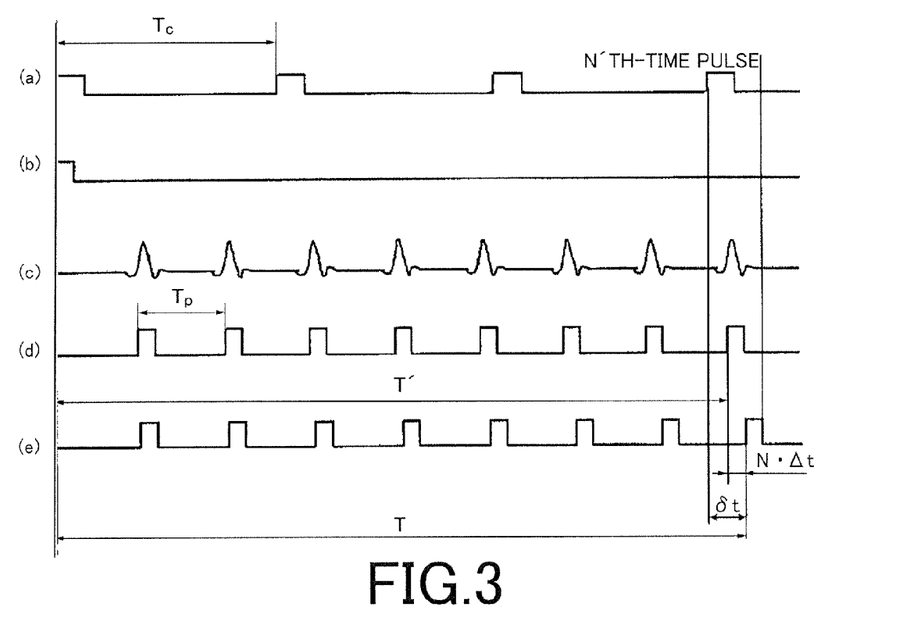

FIG. 3 is a timing chart of examples of various signals obtained in the examining device 10.

(a) illustrates a frequency-divided signal of a clock signal used in the control/processing unit 28, and (b) illustrates a start-up driving pulse produced by the control/processing unit 28. The start-up driving pulse is produced in synchronization with the frequency-divided signal of the clock signal illustrated in (a). (c) illustrates the light receiving signal output from the photo-receiver 16 and amplified, (d) illustrates the rectangular pulse produced by the comparator 20 in the absence of the light absorption, while (e) illustrates the rectangular pulse produced by the comparator 20 in the presence of the light absorption In (a) to (e) of FIG. 3, it is assumed that $T_c$ is a period of the frequency-divided signal and $T_p$ is one period in the absence of the light absorption.

As illustrated in (e) of FIG. 3, using the pulse of the clock signal, the control/processing unit 26 measures a time $\delta t$ from a rise of the N'th-time pulse to a rise of the initial rectangular pulse (Nth-time rectangular pulse) generated from then on. The elapsed time T is determined by adding time $(N'-1)\cdot T_c$ between the start-up driving pulse illustrated in (b) of FIG. 3 and the rise of the N'th-time pulse to the time $\delta t$. The accumulated delay time $N\cdot \Delta t$ is determined by subtracting the elapsed time T' in the absence of the light absorption from the elapsed time T. The delay time $\Delta t$ is computed from the accumulated delay time $N\cdot \Delta t$, and the concentration of the gas component is determined by examining the infrared radiation absorption of the gas component using the delay time $\Delta t$. At this point, the concentration of the gas component of the examination object is determined using the delay time $\Delta t$ and the previously stored reference table representing the relationship between the delay time and the concentration of the gas component.

Figure 4:
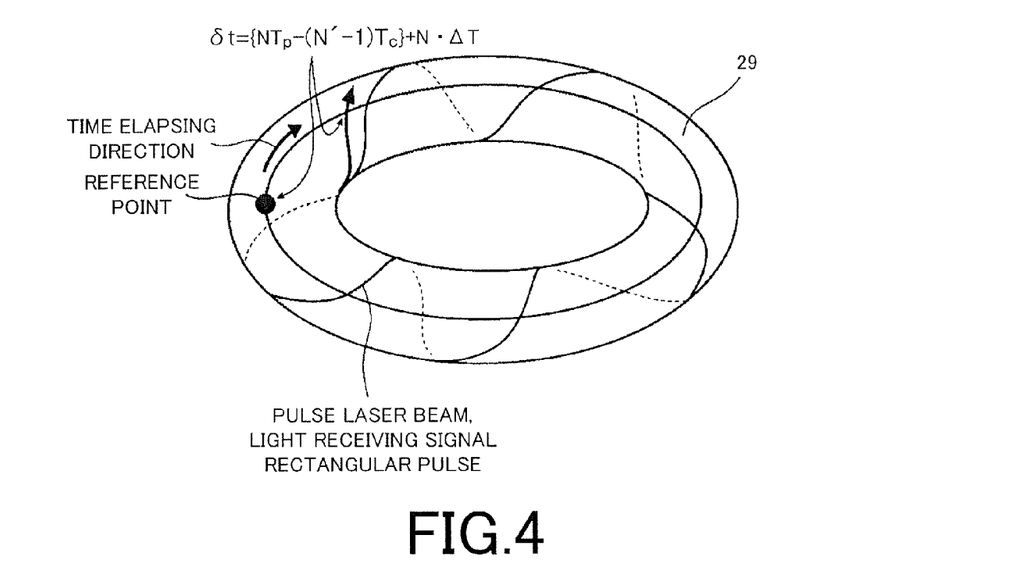
FIG. 4 is a view explaining a delay time of a rectangular pulse in the device illustrated in FIG. 1.

FIG. 4 is a view easily explaining the above-described contents. The pulse laser beam, the light receiving signal, and the rectangular pulse move spirally on a torus surface 29 illustrated in FIG. 4 such that the delay time $\Delta t$ occurs when the pulse laser beam, the light receiving signal, and the rectangular pulse make one revolution around a circular section of the torus surface 29. Therefore, the accumulated delay time $N\cdot \Delta t$ is determined when the pulse laser beam, the light receiving signal, and the rectangular pulse make N-time revolutions around the circular section.

The reason the control/processing unit 28 examines the light absorption of the gas component using the information on the delay in the time the rectangular pulse is produced, which occurs by the reduction of amplitude of the light receiving signal, is that the accumulated delay time $N\Delta t$ is measured with accuracy higher than that of the reduction of the light intensity of the pulse laser beam by the infrared radiation absorption of the gas component. For example, the infrared radiation absorption can be examined with extremely high accuracy by setting N to tens thousands times. When the number N is increased, a variation of an average value comes close to zero even if the time the rectangular pulse is produced varies, so that the one-time delay time Δt can be determined with high accuracy.

In order to measure the concentration of the gas component in the conventional methods illustrated in FIGS. 7 and 8, it is necessary to lengthen the optical path by utilizing the plural-time reflection. On the other hand, in the embodiment, the signal passes through the same optical path many times via the electric circuit. At this point, in the embodiment, one pulse laser beam passes through the cylindrical vessel of the measuring unit 14 only once. Therefore, the laser beam whose light flux is narrowed can be passed at the desired position while the light flux of the laser beam does not expand by the increased optical path length. When the length in the laser beam traveling direction of the cylindrical vessel of the measuring unit 14 is set to several centimeters, the light absorption of one pulse laser beam by the gas component (the concentration of the ppm order) having the dilute concentration is in a slight amount. At this point, the 12- to 16-bit AD converter cannot detect the difference between the light receiving signal output from the photo-receiver 16 and the light receiving signal in the absence of the light absorption. The difference cannot be obtained even if the averaging processing is performed. This is because the change of the light receiving signal by the light absorption is infinitesimal to an extent that the change of the light receiving signal cannot be captured within a significant-digit range of the AD converter. In the embodiment, the measurement of the amplitude of the light receiving signal is not used unlike the conventional method, but the high-accuracy time measurement is used, which allows the light absorption amount to be correctly measured.

In the embodiment, the control/processing unit 28 measures the time δt using the pulse of the correct clock signal. Alternatively, the time δt can be measured as follows. A triangular wave signal is started rising at the time the N'th-time pulse illustrated in (a) of FIG. 3 rises, and the time δt illustrated in (e) of FIG. 3 is measured using the signal level of the triangular wave signal when the Nth-time rectangular pulse rises. The elapsed time T may be determined by adding time $(N'-1) \cdot T_c$ to the measured time δt.

Figure 5:
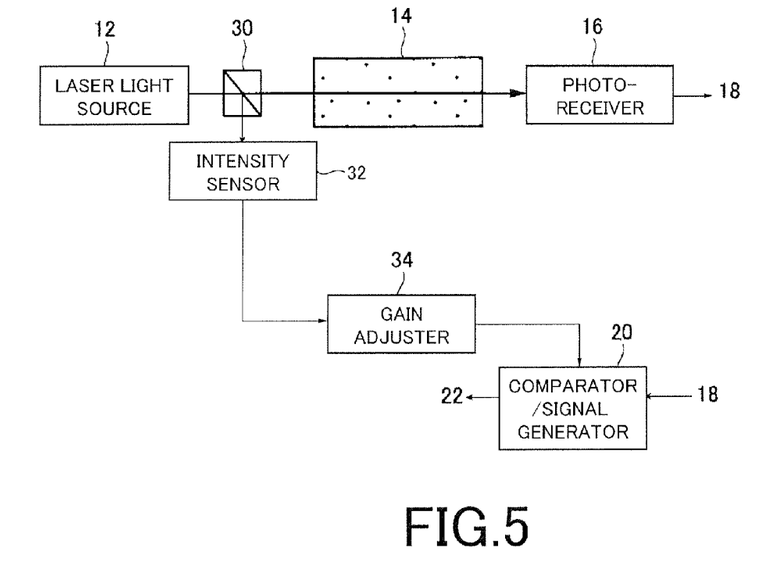
FIG. 5 is a schematic configuration diagram of a device incorporated in the device illustrated in FIG. 1.

When the light intensity of the pulse laser beam varies every time the laser light source 12 emits the pulse laser beam, or when the wavelength of the pulse laser beam is changed within the set range, the variation in light intensity can be compensated by adding a device configuration illustrated in FIG. 5. That is, a beamsplitter 30, an intensity sensor 32, and a gain adjuster (threshold adjusting unit) 34 may be provided. The beamsplitter 30 separates the pulse laser beam emitted from the laser light source 12 before the pulse laser beam incident to the measuring unit 14. The intensity sensor 32 receives the separated pulse laser beam to detect the light intensity of the pulse laser beam. In order to compensate a fluctuation of the light intensity of the pulse laser beam, the gain adjuster 34 adjusts the threshold used in the comparator 20 based on the light intensity obtained by the intensity sensor 32.

The pulse laser beam is separated with the beamsplitter 30, the light intensity of one of the separated pulse laser beams is monitored with the intensity sensor 32, and the threshold used in the comparator 20 is adjusted using the information on the light intensity obtained by the intensity sensor 32. The gain adjuster 34 sets the threshold such that the threshold is proportional to the light intensity obtained by the intensity sensor 32. Therefore, the delay time can be kept constant in the comparator 20 even if the light intensity of the pulse laser beam is changed every time of the emission. Since a noise included in the pulse laser beam emitted from the laser light source 12 is actually larger than noise included in the light receiving signal amplifier 18 and driving signal amplifier 26, the delay time can be kept constant in the comparator 20 even if the light intensity of the pulse laser beam is changed by the noise included in the pulse laser beam.

As described above, when the difference between the accumulated delay time at the first wavelength and the accumulated delay time at the second wavelength is used as the original accumulated delay time, the light intensity of the pulse laser beam may be changed between the first wavelength and the second wavelength. In such a case, as described above, the threshold used in the comparator 20 is preferably adjusted using the information on the light intensity of the pulse laser beam.

In the examining device 10, the single pulse laser beam is emitted from the laser light source 12 using the start-up driving pulse (see (b) of FIG. 3) that is produced to start the emission of the pulse laser beam, and the pulse laser beam transmitted through the gaseous body containing the gas component of the measuring object is received, thereby obtaining the light receiving signal.

The single rectangular pulse (see (d) of FIG. 3) is produced at the time the signal level of the obtained light receiving signal intersects the set threshold. After the produced rectangular pulse is amplified by the driving signal amplifier 26, the rectangular pulse is supplied as the driving pulse to the laser light source 12 in order to emit the pulse laser beam.

The laser light source 12 repeatedly emits the pulse laser beam, and the accumulated delay time NΔt is determined. The delay time represents a delay in the production timing of the rectangular pulse which occurs during a period between the latest rectangular pulse when the number of repetition times of the produced rectangular pulse reaches the N times and the start-up driving pulse illustrated in (b) of FIG. 3. The infrared radiation absorption of the gas component is examined using the accumulated delay time NΔt.

In the examining device 10 and the examining method, the emission time of the pulse laser beam is assumed one nanosecond, the period in which the signal runs in a cycle around the examining device 10 is assumed ten nanoseconds, and N is set to $10^6$ times. In such a case, ten milliseconds are required to measure the accumulated delay time N·Δt. Furthermore, when the optical path of the cylindrical vessel of the measuring unit 14 is set to 1 mm, the total of the optical path of the measuring unit 14 will be up to 1 km, and the pulse laser beam passes through the optical path length that is equal to or more than that of the conventional measuring method. That is, the light absorption amount can be obtained in a condition of the 1 km optical path length and the measuring time of ten milliseconds, so that the infrared radiation absorption amount of the gas component contained in the gaseous body can be examined in substantially real time.

Not only the invention is applied to the trace gas examining device in which the infrared radiation absorption method is adopted, but also a cross sectional distribution of molecular particles or molecular groups as well as a cross sectional distribution of molecular particles or radical particles can be determined by examining the infrared radiation absorption. The molecular particles or radical particle absorb the infrared radiation in plasma or combustion flame. The molecular particles or molecular groups absorb the infrared radiation in a solid-state surface.

Figure 6:
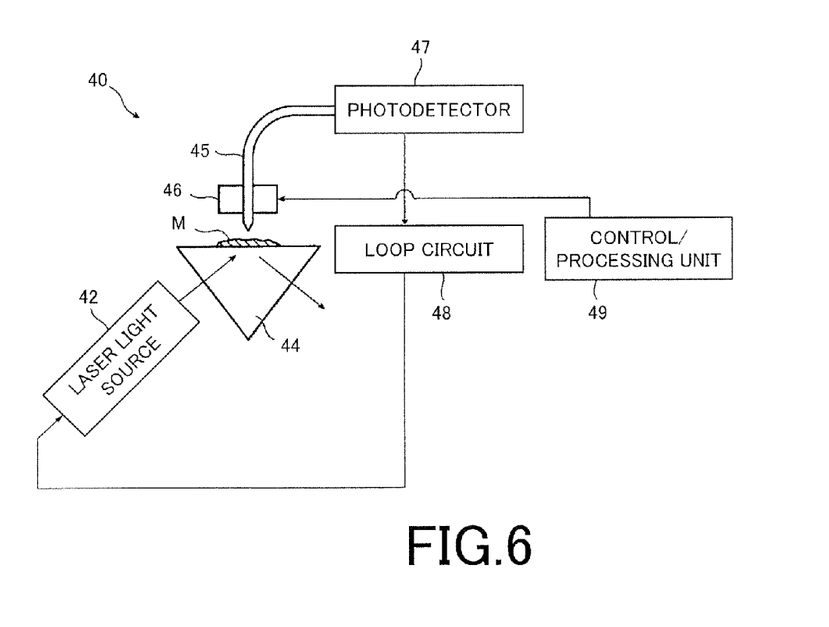
FIG. 6 is a schematic configuration diagram of a light absorption examining device according to another embodiment of the invention.

For example, the invention can suitably be applied to local infrared radiation absorption measurement like a scanning near-field microscope illustrated in FIG. 6.

FIG. 6 is a schematic configuration diagram of a scanning near-field microscope (hereinafter referred to as microscope) 40.

The microscope 40 includes a laser light source 42, a prism 44, an optical fiber 45, a PZT scanning mechanism 46, a photodetector 47, a loop circuit 48, and a control/processing unit 49.

The laser light source 42 emits the pulse laser beam having wavelength thereof in the infrared region.

The prism 44 is configured such that the laser beam emitted from the laser light source 12 is completely reflected by a bottom surface on which a measuring object M is placed.

The optical fiber 45 collects the light transmitted through the measuring object M in evanescent light that leaks from the bottom surface of the prism 44, and sends the light to the photodetector 47.

The PZT scanning mechanism 46 moves and scans a leading end of the optical fiber 45 along the bottom surface of the prism 44 such that the optical fiber 45 collects the transmitted light of the evanescent light at each position of the measuring object M placed on the bottom surface of the prism 44.

The photodetector 47 converts the light sent from the optical fiber 45 into a light receiving signal. The obtained light receiving signal is sent to the loop circuit 48.

The loop circuit 48 includes circuits similar to the light receiving signal amplifier 18, comparator 20, first coupler 22, second coupler 24, and driving signal amplifier 26 illustrated in FIG. 1. The loop circuit 48 produces the rectangular pulse at the time the light receiving signal obtained by the photodetector 47 intersects a set threshold, and amplifies the rectangular pulse to supply the rectangular pulse to the laser light source 42.

The control/processing unit 49 exerts the function similar to that of the control/processing unit 28 illustrated in FIG. 1. Accordingly, the control/processing unit 49 determines the delay time Δt of the rectangular pulse, and the control/processing unit 49 can determine an infrared radiation absorption amount of the measuring object M. The infrared radiation absorption amount is determined while the scanning is performed with the PZT scanning mechanism 46, which allows a distribution of the infrared radiation absorption to be determined. Therefore, the control/processing unit 49 can obtain a distribution (image) of a specific material that is contained in the measuring object M and absorbs the infrared radiation, and works as the microscope 40. Thus, the distribution of the specific material that absorbs the infrared radiation can be obtained.

The device and method of examining the light absorption of the invention is described above in detail. However, the invention is not limited to the embodiments, but various modifications and changes can be made without departing from the scope of the invention.

Explanations of Reference Numerals
10 examining device
12 and 42 laser light source
14 measuring unit
16 photo-receiver
18 light receiving signal amplifier
20 comparator/signal generator
22 first coupler
24 second coupler
26 driving signal amplifier
28, 49 control/processing unit
29 torus surface
30 beamsplitter
32 intensity sensor
34 gain adjuster
40 scanning near-field microscope
44 prism
45 optical fiber
46 PZT scanning mechanism
47 photodetector
48 loop circuit
50 and 60 device
51 cell
52 mirror
53, 54 detector
61 space
62, 63 concave mirror
64 detector

What is claimed is:

1. A light absorption examining device that examines pulse laser beam absorption when a measuring object is irradiated with a pulse laser beam and the pulse laser beam is transmitted through the measuring object, the light absorption examining device comprising:

a laser light source that emits the pulse laser beam according to a supplied driving pulse;

a measuring unit that retains the measuring object and irradiates the measuring object with the pulse laser beam to cause the pulse laser beam to transmit through the measuring object;

a light receiving unit that receives the pulse laser beam transmitted through the measuring object and outputs a light receiving signal;

a pulse generator that produces a single rectangular pulse of an electrical signal at a time when a signal magnitude of the light receiving signal output from the light receiving unit becomes equal to or higher than a set threshold value;

a laser driver that supplies the produced rectangular pulse as the driving pulse to the laser light source in order to drive the laser light source to emit the pulse laser beam from the laser light source every time the produced rectangular pulse is supplied to the laser light source, and drives the laser light source to emit a single pulse laser beam; and a control/processing unit that measures and determines an accumulated delay time and examines absorption of the pulse laser beam by the measuring object using the measured accumulated delay time, the accumulated delay time representing a delay in a production timing of the rectangular pulse caused by reduction of light intensity due to absorption of the pulse laser beam during a period between a start-up driving pulse and a latest rectangular pulse of an electrical signal that is produced when the pulse generator repeats to generate the rectangular pulse no less than predetermined repetition times, after the start-up driving pulse for starting the emission of the pulse laser beam is supplied to the laser driver to drive the laser light source to emit the pulse laser beam and the rectangular pulse is supplied a plurality of times from the pulse generator to drive the laser light source to emit the pulse laser beam the plurality of times.

2. The light absorption examining device according to claim 1, wherein
the measuring object is gas contained in a gaseous body,
the control/processing unit includes a reference table representing a correspondence relationship between a concentration of the gas and a delay time in the production timing of the rectangular pulse when light is absorbed by the gas, and
the control/processing unit computes the concentration of the gas from the determined accumulated delay time using the reference table.

3. The light absorption examining device according to claim 1, wherein
the control/processing unit controls a wavelength of the laser beam emitted from the laser light source to be variable,
the control/processing unit sets a first wavelength in which the accumulated delay time is maximized and a second wavelength in which the accumulated delay time is minimized to the laser light source, and
the control/processing unit examines infrared radiation absorption by the measuring object using a difference between the accumulated delay time determined at the first wavelength and the accumulated delay time obtained at the second wavelength.

4. The light absorption examining device according to claim 1, further comprising:
a beamsplitter that splits the pulse laser beam emitted from the laser light source before the pulse laser beam is incident to the measuring unit;
an intensity sensor that receives the split pulse laser beam to sense light intensity of the pulse laser beam; and
a threshold adjusting unit that adjusts the threshold in order to compensate a fluctuation of the light intensity of the pulse laser beam based on the light intensity obtained in the intensity sensor.

5. The light absorption examining device according to claim 4, wherein
the threshold adjusting unit sets the threshold such that the threshold is proportional to the light intensity obtained in the intensity sensor.

6. The light absorption examining device according to claim 1, wherein
the pulse laser beam is a laser beam having wavelength in an infrared region.

7. A light absorption examining method of examining pulse laser beam absorption when a measuring object is irradiated with a pulse laser beam and the pulse laser beam is transmitted through the measuring object, the light absorption examining method comprising:
a first step of driving a laser light source to emit the pulse laser beam using a driving pulse supplied to emit the pulse laser beam and of receiving the pulse laser beam transmitted through the measuring object to obtain a light receiving signal;
a second step of producing a single rectangular pulse of an electrical signal at a time when a signal magnitude of the obtained light receiving signal becomes equal to or higher than a set threshold value;
a third step of supplying the produced rectangular pulse as the driving pulse to the laser light source in order to emit the pulse laser beam; and
a fourth step of repeating the first step, the second step, and the third step to measure and determine an accumulated delay time, and of examining absorption of the pulse laser beam by the measuring object using the measured accumulated delay time, the accumulated delay time representing a delay in a production timing of the rectangular pulse caused by reduction of light intensity due to absorption of the pulse laser beam during a period between a start-up driving pulse and a latest rectangular pulse that is produced when the pulse generator repeats to generate the rectangular pulse signal no less than predetermined repetition times.

8. The light absorption examining method according to claim 7, wherein
a first wavelength in which the accumulated delay time is maximized and a second wavelength in which the accumulated delay time is minimized are set to the laser light source in the first step, and
infrared radiation absorption by the measuring object is examined using a difference between the accumulated delay time determined at the first wavelength and the accumulated delay time obtained at the second wavelength in the fourth step.

9. The light absorption examining method according to claim 7, wherein
the pulse laser beam emitted from the laser light source is split before the pulse laser beam is incident to the measuring object in the first step, and
the light absorption examining method further comprising a fifth step of receiving the split pulse laser beam to sense light intensity of the pulse laser beam and of adjusting the threshold in order to compensate a fluctuation of the light intensity of the pulse laser beam based on the sensed light intensity.

10. The light absorption examining method according to claim 7, wherein
the pulse laser beam is a laser beam having wavelength in an infrared region.

11. The light absorption examining method according to claim 7, wherein
the measuring object is gas, and
the light absorption examining method further comprising a sixth step of computing a concentration of the gas from the determined accumulated delay time using a reference table which has been provided before the light absorption of the measuring object is examined, the reference table representing a correspondence relationship between a concentration of the gas and a delay time in the production timing of the rectangular pulse when light is absorbed by the gas.

* * * * *